(12) United States Patent
Rosen

(10) Patent No.: US 7,972,137 B2
(45) Date of Patent: Jul. 5, 2011

(54) ANTI-MICROBIAL DENTAL FORMULATIONS FOR THE PREVENTION AND TREATMENT OF ORAL MUCOSAL DISEASE

(76) Inventor: Gerald M. Rosen, Lutherville, MD (US)

( * ) Notice: Subject to any disclaimer, the term of this patent is extended or adjusted under 35 U.S.C. 154(b) by 2427 days.

(21) Appl. No.: 10/876,491

(22) Filed: Jun. 25, 2004

(65) Prior Publication Data

US 2004/0265244 A1   Dec. 30, 2004

Related U.S. Application Data

(60) Provisional application No. 60/483,236, filed on Jun. 30, 2003.

(51) Int. Cl.
*A61C 7/24* (2006.01)
*C01B 21/00* (2006.01)
*A01N 59/24* (2006.01)
*A61N 5/06* (2006.01)

(52) U.S. Cl. ............ 433/224; 106/35; 423/351; 424/49; 424/608; 514/900; 514/902; 607/88; 607/134

(58) Field of Classification Search ............... 433/224; 106/35; 423/351; 424/49, 608; 514/900; 607/88

See application file for complete search history.

(56) References Cited

U.S. PATENT DOCUMENTS

| | | | |
|---|---|---|---|
| 4,055,645 A * | 10/1977 | Scriabine | 514/248 |
| 4,370,136 A * | 1/1983 | Widman et al. | 433/217.1 |
| 4,568,535 A * | 2/1986 | Loesche | 424/435 |
| 5,380,758 A | 1/1995 | Stamler et al. | |
| 5,484,602 A | 1/1996 | Stanley et al. | |
| 5,665,077 A | 9/1997 | Rosen et al. | |
| 5,797,887 A | 8/1998 | Rosen et al. | |
| 6,087,479 A | 7/2000 | Stamler et al. | |
| 6,656,217 B1 | 12/2003 | Herzog, Jr. et al. | |
| 2003/0026849 A1 * | 2/2003 | Thomas | 424/608 |
| 2004/0202692 A1 * | 10/2004 | Shanley et al. | 424/426 |
| 2004/0254238 A1 * | 12/2004 | Garrett et al. | 514/460 |

OTHER PUBLICATIONS

Nahornyi V V, et al. "Development of Technology and Film Analysis", Farrnarseviychnyi Zhurnal (Kiev), 1994, vol. 0, No. 3, pp. 85-88; Database BIOSIS [online] BioSciences Information Service, Philadelphia, PA, US.

* cited by examiner

*Primary Examiner* — Frederick Krass
*Assistant Examiner* — Lezah W Roberts
(74) *Attorney, Agent, or Firm* — Fish & Associates, PC

(57) ABSTRACT

Compositions and methods are directed to antimicrobial compositions and articles that release ●NO from the composition and/or article in an amount effective to prevent gingival and other oral mucosal diseases.

6 Claims, 2 Drawing Sheets

ANTI-MICROBIAL DENTAL FORMULATIONS FOR THE PREVENTION AND TREATMENT OF ORAL MUCOSAL DISEASE

This application claims the benefit of U.S. provisional patent application with the Ser. No. 60/483236, which was filed Jun. 30, 2003, and which is incorporated by reference herein.

FIELD OF THE INVENTION

This invention relates generally to novel uses of nitric oxide (●NO) to deliver ●NO for the prevention and treatment of gingival and other oral mucosal diseases.

BACKGROUND OF THE INVENTION

With the discovery that the free radical ●NO mimics the physiologic property of Endothelium-Derived Relaxing Factor (EDRF) (Furchgott and Zawadzki, Nature, 288: 373-376, 1980; Palmer, et al., Nature, 327: 524-526, 1987), it has become clear that ●NO is an essential physiologic factor for maintaining normal life processes. Among the important physiologic functions of ●NO is its microbicidal activity when secreted from stimulated macrophages (see, e.g., S. H. Iyengar, et al., Proc. Natl. Acad. Sci. USA, 84: 6369-6373, 1987; Deng, et al., J. Immunol. 151: 322-329, 1993; Weisz, et al., J. Biol Chem. 269: 8324-8333, 1994; Fang, J. Clin. Invest. 99, 2818-2825; Shiloh, et al., Immunity, 10: 29-38, 1999).

However, the pharmacological applications of ●NO are limited, as systemic use can frequently result in severe toxicity. For instance, administration of ●NO systemically to treat localized abnormalities or diseases is contraindicated, because the control of its dosage in the therapeutic range cannot be easily achieved. Even if it were possible to carefully titrate the dose of ●NO to minimize systemic toxicity, it would be difficult to locally administer this gas to sites of interest. Therefore, the development of therapeutic agents, that mimic the pharmacological action of ●NO, has received considerable attention. Several classes of ●NO releasing compounds have been developed, including sydnonimine (Noack and Feelisch, J. Cardiovasc. Pharmacol. 14S: 51-55, 1989), nitroglycerin (Noack and Feelisch, J. Cardiovasc. Pharmacol. 14S: 51-55, 1989), S-nitroso derivatives (Ignarro, et al., J. Pharmacol. Exp. Ther. 218: 739-729, 1981; Kowaluk and Fung, J. Pharmacol. Exp. Ther. 255: 1256-1254, 1990; Stamler, Loscalzo, Slivka, Simon, Brown and Drazen, U.S. Pat. No. 5,380,758, 1995) and N-nitroso compounds (Maragos, et al., J. Med. Chem. 34: 3242-3247, 1991; Keefer, Dunams and Saavedra, U.S. Pat. No. 5,366,997; Keefer and Hrabie, U.S. Pat. No. 5,405,919). These compounds require either hydrolysis or metabolic activation, through either oxidation or reduction, to generate NO●. In contrast nitroprusside, a member of a family of organic metallic compounds, can release NO● through light activation (Wolf and Swinheart, Inorg. Chem. 14: 1049-1053, 1975; Bates, et al., Biochem. Pharmacol. 42S: S157-S165, 1991).

Therefore, while the significance of ●NO in numerous medical applications is well recognized and while there are numerous methods and compositions known in the art that release ●NO, all or almost all of them have various disadvantages. Consequently, there is still a need for compositions and methods in which ●NO can be safely and effectively used in the treatment of a disease.

SUMMARY OF THE INVENTION

In one aspect, the invention relates to a method for preventing and/or treating gingival disease in a living being by coating the surface of a foreign body that contacts the gums or other oral tissue with a physiological acceptable polymer that contains dissolved or dispersed therein an amount of a nitrosyl-containing organometallic compound, which can also be an ionic salt or a chelate, that decomposes at body temperature and in the presence of light to release ●NO from the coating in an amount effective to prevent gingival and other oral mucosal diseases.

In another aspect, the invention relates to an aqueous liquid coating composition comprising (a) an aqueous vehicle; (b) an injectable physiologically acceptable polymer dissolved or dispersed in the vehicle; and (c) a nitrosyl-containing organometallic compound, which can also be an ionic salt or a chelate, that slowly decomposes at body temperature and in the presence of light to release ●NO. The polymer is precipitable from the aqueous vehicle, e.g., through evaporation of the aqueous vehicle. The concentration of the nitrosyl-containing organometallic compound, ionic salt or chelate in the aqueous vehicle is effective to generate antimicrobial activity when the polymer containing the nitrosyl-containing organometallic compound, whether an ionic salt or a chelate occluded therein is deposited in the gum of a living being.

In a further aspect, the invention relates to a dental composition of matter, preferably in the form of a film or a flexible sheet coated with a coating of a physiological acceptable polymer which is insoluble in body fluids and which contains dissolved or dispersed therein a nitrosyl-containing organometallic compound that can be an ionic salt or a chelate, and which, when implanted for minutes into the wall of the gum of a living being decomposes at body temperature after exposure to light to release ●NO in an amount and at a rate effective to prevent gingival and other oral mucosal diseases.

In a further aspect, the invention relates to a dental composition of matter, preferably in the form of a film or a flexible sheet coated with a coating of a physiological acceptable polymer which is insoluble in body fluids and which contains dissolved or dispersed therein a nitrosyl-containing organometallic compound that can be an ionic salt or a chelate and a reductant such as ascorbic acid or a thiol, and which, when implanted for minutes into the wall of the gum of a living being decomposes into a gel at body temperature and releases ●NO in an amount and at a rate effective to prevent gingival and other oral mucosal diseases. The reductant is preferably exogenous to the patient.

Various objects, features, aspects and advantages of the present invention will become more apparent from the following detailed description of preferred embodiments of the invention.

DETAILED DESCRIPTION

Figure 1:
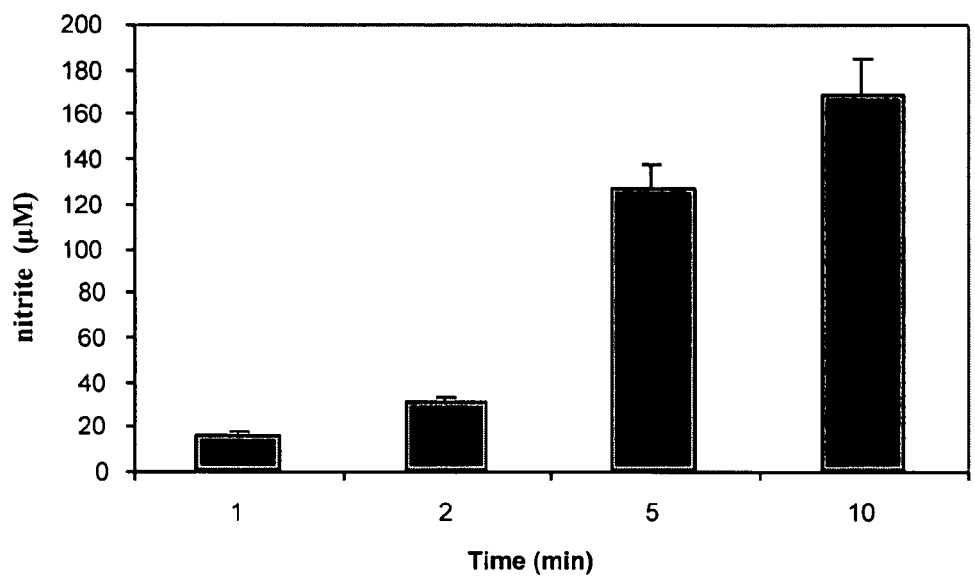
FIG. 1 is a graph depicting ●NO concentration after exposure of exemplary films to light.

The invention is based on the delivery of ●NO from a coating in an amount effective to kill microbes that would otherwise result in gingival and other oral mucosal diseases. The coating includes a nitrosyl-containing organometallic compound such that the compound within the coating is stable at room temperature but at body temperature and in the presence of light releases ●NO from the coating. As used herein, the term "nitrosyl-containing organometallic compound" includes ionic salts and chelates. The method allows for the local delivery of ●NO at concentrations at the surface of the gum that cannot be achieved safely by the administration of a nitrosyl-containing organometallic compound, including ionic salts or chelates, systemically, whether by applying the compound itself, by intramuscular injection or by injection directly into the blood vessel.

An example of such a nitrosyl-metal chelate is nitroprusside in the form of, for example, sodium nitroprusside. The iron ion of the nitroprusside is complexed to five cyano groups. The sixth ligand position of the iron ion is occupied by a nitrosyl group. When a polymer having nitroprusside encapsulated therein is exposed to an aqueous solution and light, it decomposes to release ●NO (e.g., SNP in an aqueous solution upon exposure to light releases ●NO, as detailed in Wolfe and Swinehart, Inorgan. Chem. 14, 1049-1053, 1975). The enhanced stability of nitroprusside in the polymer compared to its short lifetime in blood is the result of the inability of compounds such as reductants, for example, thiols and ascorbic acid, to interact with the nitroprusside by, for example, diffusing through small pores or the surface of the polymer. Diffusion of these compounds into the polymer would inactivate the nitroprusside by rapid decomposition and release of ●NO. In some cases, however, it is desirable to include a reductant such as ascorbic acid or a thiol, to promote the release of ●NO in the absence of light.

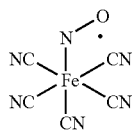

Structure of Nitroprusside

Other suitable complexing agents for the iron ion that can take the place of the cyano groups of nitroprusside include, for example, ethylenediaminetetraacetic acid (EDTA), diethylenetriaminepentaacetic acid (DTPA), and other members of this class of chelates; 1,4,7,10-tetraazacyclododecane-N,N', N'',N'''-tetraacetic acid (DOTA), trans-1,2-cyclohexylenediamine-N,N,N',N'-tetraacetic acid and other members of this class of chelates; as well as other chelates.

This invention relates to methods, compositions and articles of manufacture useful in the prevention of gingival disease. By impregnating a polymer with a nitrosyl-containing organometallic compound, ●NO can be locally delivered at a dose and at a rate that can be controlled by varying, for example, the concentration of the nitrosyl-containing organometallic compound in the polymer, the nature of the polymer forming the coating, and the amount of time the polymer with the nitrosyl-containing organometallic compound dispersed therein is exposed to light. With such an approach, systemic ●NO toxicity can be avoided.

Nitrosyl-containing organometallic compounds useful in the composition are those which, when used according to the methods of the invention, are:

(a) non-toxic, that is, substantially free from any significant toxic effects at their effective applied concentration;

(b) substantially free of symptomology, that is, they do not produce significant symptoms detectable to the person treated at their effective applied concentration; and (c) relatively stable at room temperature in an aqueous environment away from light, i.e., once a nitrosyl-metal chelate is impregnated into a polymer, ●NO is not released therefrom at a significant rate, e.g., during the preparation of the coating or during self storage in a packaged container, the nitroprusside does not decompose at a rate greater than 0.1% per month.

The nitrosyl-containing organometallic compound, can be a compound of the formula $[MX_5NO]^{-2} Y^{+2}$ or $2Y^{+1}$ where M is a transition metal such as Fe, Co, Mn, Ru; X is a negatively a charged ion such as CN, Cl, Br, I, or one or more of the X ligands can be chelates such as EDTA, DTPA that, at physiologic pH, have negatively charged carboxylate groups; and Y is a positively charged ion, such as and alkali metal or alkaline earth, for example, $Na^+$, $K^+$ or similar monovalent cations or divalent cations.

Coatings according to the invention can be from 0.1-1.0 mm thick and contain 1 μmole per $mm^2$ to 100 μmoles per $mm^2$ of the nitrosyl-containing organometallic compound. Higher concentrations are desirable when the diffusion rate of ●NO from the polymer is very slow or when it is desirable to release higher concentrations of ●NO, for example if the microorganisms are resistant to the killing by low levels of ●NO. As used herein, "coatings" can refer to a coating on a substrate such as a sheet, for example a plastic sheet or flexible sheet of thin metal; or may refer to a sheet comprising a polymer formed on a surface having the nitrosyl-containing organometallic compound dissolved or dispersed therein that is subsequently peeled away from the surface. In further contemplated aspects, the coating may also be directly applied to a tooth or gingival tissue.

A wide variety of polymers can be used to encapsulate nitroprusside or other nitrosyl-containing organometallic compounds in forming the coatings of the invention. Polymers include physiologically inert polymers, biodegradable polymers, polymers that are only slowly soluble, and polymers that are insoluble in blood. Suitable insoluble polymers include those that form a permeable membrane coating so that ●NO can migrate from the coating as the ●NO is produced. Suitable biodegradable polymers that can be used as drug delivery systems include natural polymers, for example (1) collagen, (2) albumin, (3) casein, (4) fibrin and (5) gelatin (S. Bogdansky, in: *Biodegradable Polymers as Drug Delivery Systems*, ed. by M. Chasin and R. Langer, Marcel Dekker,. Inc. New York, pp. 231-259, 1990). Synthetic polymers suitable in forming the coatings of the invention include: (1) polylactide and polyglycocide (D. H. Lewis, in: *Biodegradable Polymers as Drug Delivery Systems*, ed. by M. Chasin and R. Langer, Marcel Dekker,. Inc. New York, pp. 1-42, 1990); (2) polyvinyl alcohols (P. R. Byron and R. N. Dalby, *J. Pharm. Sci.* 76: 65-67, 1987); and (3) polyalkylene oxides such as polyvinyl chloride.

Coatings of the invention can be applied to a foreign body, for example a medical device that can be inserted or permanently implanted into a living being, for example a human. When the foreign body is inserted into the living being, it preferably is physiologically inert and, when permanently implanted, also biodegradable. Alternatively, the invention exists as a polymer sheet that includes a nitrosyl-containing organometallic compound dissolved or dispersed therein.

In use, it is contemplated that the coating (e.g., in form of a sheet or coated foreign body) is placed in the mouth of a living being during a dental procedure such as dental surgery. For example, the coating can be placed against a gum or into a tooth socket after a tooth is extracted. Once in place, the coating is illuminated with light initiating the release of ●NO. The nitric oxide thus released acts as an anti-microbial to kill bacteria at and around the site where the coating is placed, effectively sterilizing the site where the procedure is being performed. Additional procedures or surgery can then continue. For example, after a tooth socket has been sterilized, an implant can be placed in the tooth socket. This use thus allows for the procedure to proceed with gingival or other oral mucosal disease being prevented or treated.

EXAMPLES

Preparation of ●NO Delivery System

A 5% (w/w) of polyvinyl alcohol (PVA, 99% hydrolyzed, M.W. 124,000-186,000) solution was prepared by dissolving PVA in distilled water at 100° C. After this PVA solution was prepared, it was cooled to room temperature and nitroprusside, as sodium nitroprusside (SNP), was added to reach a final concentration of 10 mM. A solution of polyvinyl chloride (PVC) (prepared by dissolving PVC in THF, 5% w/w) was placed over a glass plate and air-dried. This dried PVC film was coated with either PVA-containing SNP or PVA-without SNP and allowed to air dry in the dark. Then a solution of PVC (5%, w/w in THF) was again placed over the dried PVA-containing SNP/PVC film. In this manner, SNP, which was incorporated into PVA, is sandwiched between two layers of PVC, creating a thin film. At this point, these two-types of films, PVC/PVA-containing SNP and PVC/PVA without SNP were used to estimate ●NO release and measure microbicidal activity.

Assay for ●NO

The Griess Reaction was used to estimate ●NO concentration after exposure of the two types of films prepared according to Example 1, i.e. PVC/PVA-containing SNP and PVC/PVA without SNP, to light. For these experiments 1-cm×1-cm squares of each film (n=3) were cut, placed into a solution of 2 mL of pH 7.4 sodium phosphate buffer, and exposed to light from a slide projector for various times. After which the films were removed and the remaining solution was exposed to air for 24 hr. A sample of the phosphate buffer (0.6 mL) was removed and added to the freshly prepared Griess reagent (0.4 mL of 0.1% N-(1-naphthyl)ethylenediamine in water and 1% sulfanilamide in 5% phosphoric acid mixed 1:1). This reaction was incubated for 15 min at room temperature and absorbance was recorded at 550 nm. Concentrations of nitrite were estimated by comparing absorbances at 550 nm against standard solutions of sodium nitrite prepared in the same buffer (Green, et al., Anal. Biochem. 126: 131-138, 1982) Data are presented in FIG. 1.

Microbicidal Activity Assay of ●NO

Experiments were undertaken to evaluate the microbicidal properties of ●NO released from sodium nitroprusside incorporated into a PVC/PVA film, which is then exposed to light. In Phase 1, preliminary studies were performed in order to determine the appropriate testing procedures for light activated ●NO release and its antimicrobial properties. The selected test organism was *Pseudomonas aeruginosa* (ATCC 15542). This selection was based on its usefulness in AOAC protocols to determine disinfection and effects of antimicrobial agents. Knowing that *Pseudomonas aeruginosa* grows in a slime layer, allowed for evaluation of the usefulness of the PVC/PVA film containing sodium nitroprusside and the ability of ●NO released into a semi-liquid medium, as might be found in the oral cavity. In addition, various sources of light were evaluated. A high intensity dental light, which is often used in the curing of composite materials in the dentist's office was initially evaluated. In addition, standard incandescent bulb light with a shield to focus the light to a localized area was also evaluated. All experiments were performed in duplicate by overlapping procedures so that the procedure was repeated at least one time in addition to adding other techniques. In Phase 2, time, medium, organism and conditions of exposure were selected from the preliminary trials and evaluated regarding antimicrobial effects of released NO● from the PVC/PVA film.

In a typical phase 2 experiment, MH plates (100×15 mm, 8 cm in diameter) were divided in half and labeled side A and side C. Plates were inoculated with 500 ml of the microbial suspension (~1.0×10$^5$ CFU/ml) and spread plated to cover the agar plate. An additional plate was spread plated and incubated undisturbed (control). Pre-cut sections of film A and film C were placed on their appropriate side. The negative (no light) control was placed under a box to restrict light exposure. All of the test plates were labeled individually for 3 or 5 min (representing the time of exposure to the light). Post-exposure, all plates were incubated at 37° C. for 24 hr., the PVC film removed, the clear zone, if any, evaluated and placed back in the incubator. The evaluation was repeated at 48 hr.

Figure 2:
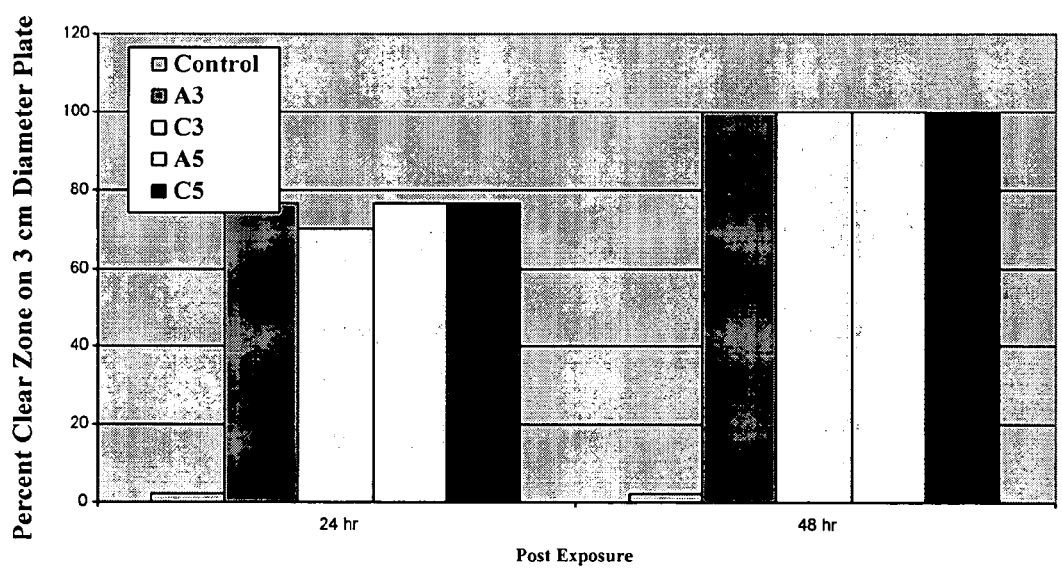
FIG. 2 is a graph depicting microbicidal activity of ●NO in an in vitro assay.

All plates exposed to ●NO released from sodium nitroprusside incorporated into a PVC/PVA film, demonstrated a clear outlined square where the film had been placed and extending beyond. By 48 hr the treatment zones extended to include 100% of the plates. The control film and inoculum control showed the characteristic light green color usually associated with *Pseudomonas aeruginosa* and its growth on Mueller Hinton agar. Results are graphically depicted in FIG. 2. These data at 24 hr and 48 hr were interpreted to indicate microbial killing associated with the released ●NO from sodium nitroprusside incorporated into a PVC/PVA film.

Figure 3:
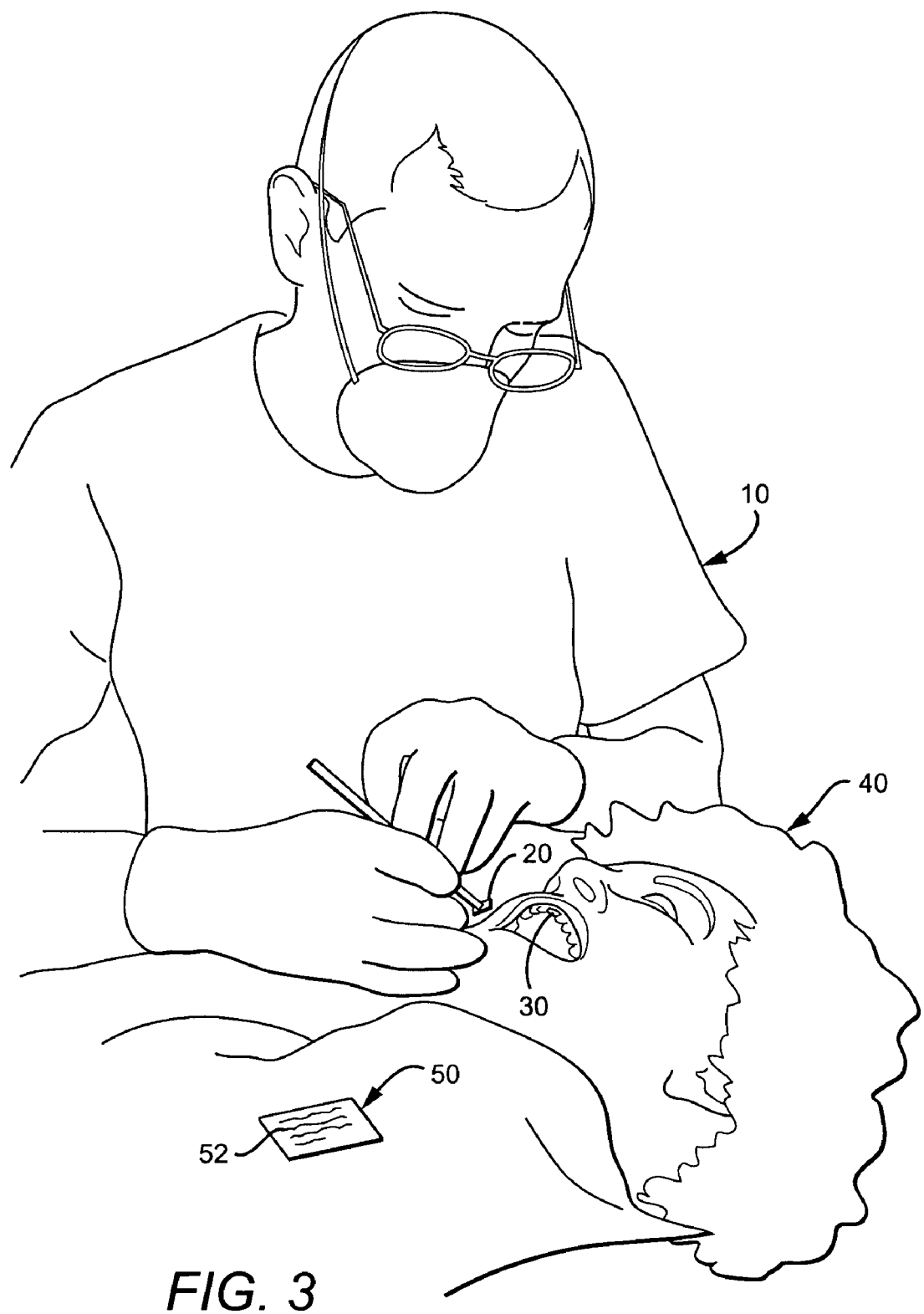
FIG. 3 is a perspective view of a dentist inserting a ●NO releasing film into a cavity in the gum of a patient.

In FIG. 3, a dentist 10 is inserting a ●NO releasing film 20 into a cavity 30 in the gum of a patient 40. To the side is a packaging 50 from which the film was removed, the packaging having text 52 instructing use of the film for dental use. The term "dentist" is used here as a euphemism to indicate any person performing dental work, including someone having a dental degree and license, a veterinary degree if the patient is an animal, a licensed or non-licensed assistant, dental student, and so forth. The term "dental use" should be similarly broadly construed.

In general, the dentist would produce a cavity 30 in the gum of a patient, such as by extraction of a tooth, or by removal of other tissue such as occurs in a root canal operation. The term "film" here is used to mean any relatively thin piece, especially one not more than 5 mm in thickness. Of course it may be that the dentist did produce the cavity him/herself. The cavity may have been produced as a natural course of a disease process, through a traumatic accident, by an assistant, or in some other manner.

It is possible that the film would be marketed in small squares or other shapes, and the dentist would simply select one or more pieces from a container. Alternatively, the dentist could cut a larger piece of film 20 into a suitable smaller size. Scissors could be used to sever the film into an appropriately sized piece, or the film could be segmented, torn, or severed in some other manner.

The next step is to introduce the film into the cavity 30. This could be accomplished in any suitable manner, introducing the film as a thin sheet, or as a folded or crumpled sheet, or indeed as a pellet. At this point there are two distinct procedures that could be followed. In one procedure the dentist waits until it is expected that a suitable amount of ●NO has been released from the film, removes the film from the cavity, and closes the cavity. Alternatively, the dentist could insert a dissolving form of film into the cavity, and then suture or otherwise close the cavity with the film inside. In either case it is contemplated that the film would release sufficient ●NO to effectively treat a microorganism promoted gingival disease by significantly reducing the prevalence of active microorganisms. In some instances the dentist may choose to shine a light onto the film, which light would trigger rapid release of ●NO from the film. If a light is not used, release of the ●NO could be triggered by enzymes or other components naturally present in the mouth.

The film can utilize any suitable ●NO releasing material, but preferably uses a nitrosyl-containing organometallic compound, which may advantageously be present as an ionic salt or a chelate. The most preferred ●NO releasing material is a nitroprusside salt such as sodium nitroprusside.

Thus, specific embodiments and applications of anti-microbial dental formulations for the prevention and treatment of oral mucosal disease have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method for the treatment of gingival disease resulting from exposure of microorganisms in a living being, comprising:
   providing a flexible film having a composition that dissolves in the mouth of a patient and releases an amount of nitric oxide (●NO) effective to treat a microorganism promoted gingival disease;
   producing a cavity in the gum of a patient;
   plugging the cavity with an amount of the film; and
   closing the cavity.

2. The method according to claim 1, wherein the composition is a nitrosyl-containing organometallic ionic salt or a chelate.

3. The method of claim 1, further comprising the step of activating the film with light.

4. The method of claim 1 wherein the composition comprises a nitrosyl-containing organometallic compound.

5. The method of claim 1 wherein the nitrosyl-containing organometallic compound comprises nitroprusside.

6. The method of claim 1, further comprising removing the film from the cavity before closing the cavity.

* * * * *